US00PP28656P3

(12) United States Plant Patent
Carruth

(10) Patent No.: US PP28,656 P3
(45) Date of Patent: Nov. 21, 2017

(54) SHRUB ROSE PLANT NAMED 'WEKSOLCIBARKO'

(50) Latin Name: *Rosa hybrida*
Varietal Denomination: WEKsolcibarko

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 22 days.

(21) Appl. No.: 14/757,109

(22) Filed: Nov. 19, 2015

(65) Prior Publication Data

US 2017/0150660 P1 May 25, 2017

(51) Int. Cl.
*A01H 5/02* (2006.01)

(52) U.S. Cl.
USPC ..... Plt./107

(58) Field of Classification Search
USPC ..... Plt./101, 107
See application file for complete search history.

(56) References Cited

U.S. PATENT DOCUMENTS

PP17,346 P2 1/2007 Radler

OTHER PUBLICATIONS

"HelpMeFind"—'Weksolcibarko' website—http//www.helpmefind.com/gardening/l.php?i=2.72447 Retieved from the Internet on Jan. 31, 2017. (1 page total).*

* cited by examiner

*Primary Examiner* — Susan McCormick Ewoldt
(74) *Attorney, Agent, or Firm* — McKee, Voorhees & Sease, PLC

(57) ABSTRACT

A new variety of Shrub rose suitable for garden decoration, having flowers of yellow gold blushing pink coloration.

1 Drawing Sheet

Classification: The present invention relates to a new *Rosa hybrida* plant.

Variety denomination: The new plant has the varietal denomination 'WEKsolcibarko'.

BACKGROUND OF THE INVENTION

This invention relates to a new and distinct variety of Shrub Rose. It has a non-disseminated seedling of my creation as its seed parent with the following genetic origin {[Zorina×(*Rosa soulieana*×Europeana)]×Trumpeter}×[(Playboy×Olympiad)×Baby Love] and as its pollen parent the variety known as 'RADcor' (U.S. Plant Pat. No. 17,346).

SUMMARY OF THE INVENTION

Among the features which distinguish the new variety from other presently available and commercial rose cultivars known to the inventor are the following combinations of characteristics: its high degree of resistance to black spot, powdery mildew and rust, its rough peduncle with many stipitate glands and few small prickles and its abundant bloom. The plant has a moderately spreading bushy rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKsolcibarko' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKsolcibarko' bears single flowers (about 5 to 8 petals) of yellow gold blushing pink coloration, the non-disseminated seedling bears semi-double flowers of medium yellow coloration with significantly heavier petalage (about 12 to 15 petals). The new variety has a moderately spreading bushy rounded medium height growing habit (about 98 to about 132 cm. in height), whereas the seed parent has an upright significantly taller growing habit (about 160 to about 180 cm. in height).

The new variety may be distinguished from its pollen parent, 'RADcor' by the following combination of characteristics: whereas 'WEKsolcibarko' bears medium sized flowers (about 6.1 to about 8.7 cm. in diameter) of yellow gold blushing pink coloration, 'RADcor' bears significantly smaller flowers (approximately 4.5 cm. in diameter on average) of light coral pink coloration with a yellow eye. The new variety has a moderately spreading bushy rounded medium height growing habit (about 98 to about 132 cm. in height and about 165 to about 180 cm. spread at the widest point), whereas the pollen parent has a rounded and bushy significantly shorter and more compact growing habit (approximately 100 cm. in height on average and approximately 100 cm. spread on average).

COMPARISON WITH THE CLOSEST COMMERCIALLY AVAILABLE CULTIVAR

The closest commercially available cultivar to the new variety is the pollen parent 'RADcor' (U.S. Plant Pat. No. 17,346).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers in clusters of three to ten or more per stem. Flowers are borne in regular rounded clusters on strong somewhat short to medium length stems (about 18 to about 64 cm.). The cluster ranges from about 9.2 to about 15.3 cm. in diameter. Outdoors, the plant blooms abundantly and nearly continuously during the growing season. The flowers have a moderate spicy to somewhat fruity fragrance.

BUD

The peduncle is about 2.6 to about 5.7 cm. in length, of average caliper (about 0.2 to about 0.3 cm. in diameter), and usually erect. It is rough with many stipitate glands, and few hairs and small prickles. Peduncle color is between 146B and 146C often heavily suffused, especially on the side exposed to the sun, with between 187B and 183B.

Before the calyx breaks, the bud is about 0.8 to about 1.2 cm. in diameter at the widest point, about 1.3 to about 1.7 cm. in length, and pointed in shape. The surface of the bud bears between 8 to 11 foliaceous appendages with some stipitate glands and very few hairs, usually with slender much cut foliaceous parts extending beyond the tip of the bud about ¾ or more of its length. Bud color is between 146A and 138A often heavily suffused, especially on the side exposed to the sun, with between 187B and 187A.

The sepals are about 2.1 to about 2.8 cm. in length and about 0.6 to about 0.9 cm. in width at the widest point. The outer surface color of the sepal is between 146A and 138A often heavily suffused, especially on the side exposed to the sun, with between 187B and 187A. The outer surface of the sepal is somewhat rough and bears between 0 to 5 foliaceous appendages with some stipitate glands and very few hairs. The inner surface color of the sepal is near 146B broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with some stipitate glands and hairs.

The receptacle of the flower is of moderately long length (about 0.6 to about 0.8 cm.) and average in caliper (about 0.6 to about 0.7 cm. in diameter). The receptacle is urn-shaped in form. Its surface is smooth with some hairs but rough at the base with many stipitate glands and few small prickles and with moderately thin fleshy walls. The receptacle color is between 137C and 138A often moderately suffused, especially on the side exposed to the sun, with between 187B and 187A.

As the petals open (after the calyx breaks), the bud is about 1.4 to about 2.1 cm. in diameter at the widest point, about 1.7 to about 2.7 cm. in length, and pointed to moderately ovoid in form. The color of the under surfaces of the newly opened petals is between 24C and 24B often heavily suffused on the outermost petals with between 53A and 53B. At the point where the petal attaches, there is a moderately small zone of between 13C and 14C. The color of the upper surfaces of the newly opened petals is between 14B and 13A at the base suffused toward the middle of the petal with between 53C and 53D. There is no visible change in coloration at the point where the petal attaches.

BLOOM

When fully open, the bloom ranges from about 6.1 to about 8.7 cm. in diameter. Petalage is single with about 5 to 8 petals and about 0 to 2 petaloids irregularly arranged. When partially open, the bloom form is moderately globular to cupped, and the petals are loosely spiraled to cupped with petal edges somewhat reflexed outward. When fully open, the bloom form is cupped to somewhat flat, and the petals are loosely cupped to slightly undulated with petal edges somewhat reflexed outward.

PETALS

The substance of the petals is moderately heavy and of medium to somewhat thick thickness, with upper surfaces moderately satiny and under surfaces slightly shiny. The petals are about 2.9 to about 4.3 cm. in length and about 2.3 to about 4.1 cm. in width at the widest point. Petal margins are entire.

The outer and inner petals are broadly obovate in shape with rounded apices.

Petaloids are about 1.8 to about 3.5 cm. in length and about 0.9 to about 2.5 cm. in width at the widest point. Petaloids are irregularly shaped somewhat obovate to moderately oblanceolate with rounded apices.

NEWLY OPENED FLOWER

The color at the base of the under surfaces of the outer, intermediate and inner petals is between 10B and 8B gradually suffusing toward the middle of the petal to between 27A and 27B. There is no visible change in coloration at the point where the petal attaches. The color at the base of the upper surfaces of the outer, intermediate and inner petals is between 8A and 18A gradually suffusing toward the middle of the petal to between 61B and 53C. There is no visible change in coloration at the point where the petal attaches.

The under and upper surface colors of the petaloids are similar in coloration to the upper and under surfaces of the intermediate and inner petals.

The general tonality of the newly opened flower is between 8A and 18A at the base gradually suffusing toward the middle of the petal to between 61B and 53C.

THREE-DAY-OLD FLOWER

The color at the base of the under surfaces of the outer, intermediate and inner petals is between 10D and 9D gradually suffusing toward the middle of the petal to between 36B and 49C. There is no visible change in coloration at the point where the petal attaches. The color at the base of the upper surfaces of the outer, intermediate and inner petals is between 8D and 155B gradually suffusing toward the middle of the petal to between 61B and 67B. At the point where the petal attaches, there is a moderately large zone of between 10C and 8B.

The under and upper surface colors of the petaloids are similar in coloration to the upper and under surfaces of the intermediate and inner petals.

The general tonality of the three-day-old flower is between 8D and 155B at the base gradually suffusing toward the middle of the petal to between 61B and 67B.

On the spent bloom, the petals usually drop off cleanly.

In November in Wasco, Calif., blooms on the bush growing outdoors generally last about three to four days. Cut roses from plants grown outdoors and kept at normal indoor living temperatures generally last about four to five days.

MALE REPRODUCTIVE ORGANS

Stamens are many in number (average about 100) and are arranged regularly about the pistils; a few are mixed with petaloids. The filaments are of medium to moderately long length (about 0.4 to about 1.1 cm.) most with anthers. Filaments are between 13B and 15B in color sometimes lightly suffused with near 53C. The anthers are moderately small for the class and all open approximately at the same time. Anther color when immature is near 22A on the external part and near 11D on the internal part. Anther color at maturity is near 164C on the external part and near 200A on the internal part. Pollen is moderately abundant and between 23A and 23B in color.

FEMALE REPRODUCTIVE ORGANS

Pistils vary in number (average about 45). The styles are moderately even, somewhat short in length (about 0.2 to about 0.4 cm.), moderately heavy in caliper, and somewhat tightly bunched. Stigma color is between 14C and 16C. Style color is between 2D and 4D often heavily suffused with between 53B and 53C. Ovaries are usually all enclosed in the calyx. The ovaries are of small size and between 155B and 155D in color.

Hips have not been observed on this variety when grown in Wasco, Calif.

FOLIAGE

The compound leaves are usually comprised of three to seven leaflets and are borne abundantly. The five-leaflet leaves are about 5.8 to about 12.0 cm. in length and about 4.0 to about 9.8 cm. in width at the widest point, leathery to somewhat crisp in texture on both sides, and glossy in finish on the upper side and matte in finish on the under side. The leaves have a pinnate venation pattern. The terminal leaflets are about 2.2 to about 5.5 cm. in length and about 1.8 to about 4.1 cm. in width at the widest point, shaped obovate with acute apices and rounded bases. Their margins are usually simply serrate.

The upper surface color of the mature leaf is between 139A and 137A. The under surface color of the mature leaf is between 147B and 137C. The under and upper colors of the leaf veins on the mature leaf are similar in coloration to the upper and under surfaces colors of the mature leaf The upper surface color of the young leaf is between 137A and 146B, often heavily suffused with between 187A and 187B. The under surface color of the young leaf is between 138B and 147B, often heavily suffused with between 187B and 183C. The under and upper colors of the leaf veins on the young leaf are similar in coloration to the upper and under surfaces colors of the young leaf.

The rachis is average to somewhat heavy in caliper and rough. The upper side is deeply grooved with some hairs and very few stipitate glands on the edges of the grooves. The under side of the rachis is rough with many hairs, very few stipitate glands and few small prickles. The rachis color is near 146C on the under side and near 137B on the upper side, often moderately suffused on the young leaves with between 187B and 183C.

The stipules are about 1.1 to about 1.5 cm. in length and moderately wide (about 0.6 to about 0.9 cm.) with moderately long straight points that usually turn out at an angle of more than 45 degrees and sometimes recurve toward the stem. The under and upper surface color of the stipule is between 137A and 137B. The upper and under surfaces of the stipules are smooth in texture.

The petiole is average to somewhat heavy in caliper and rough. The upper side is deeply grooved with some hairs and very few stipitate glands on the edges of the grooves. The under side of the petiole is rough with many hairs, very few stipitate glands and few small prickles. The petiole is about 0.6 to about 1.4 cm. in length and about 0.1 to about 0.2 cm in width at the widest point. The petiole color is near 146C on the under side and near 137B on the upper side, often moderately suffused on the young leaves with between 187B and 183C.

The plant displays a high degree of resistance to powdery mildew (*Sphaerotheca pannosa*), black spot (*Diplocarpon rosae*) and rust (*Phragmidium* sp.) as compared to other commercial varieties grown under comparable conditions in Wasco, Calif. The plant's winter hardiness and drought/heat tolerance are yet to be determined.

GROWTH

The plant has a moderately spreading bushy rounded medium height growing habit (about 98 to about 132 cm. in height and about 165 to about 180 cm. spread at the widest point), with full branching. It displays moderately vigorous growth and the canes are of somewhat light to medium size caliper for the class (about 1.3 to about 2.2 cm. in diameter at the widest point).

The color of the major stems is between 146A and 148A. The major stems are rough in texture and they bear some large prickles that are about 0.9 to about 1.2 cm. in length. The large prickles are angled slightly downward with a moderately long somewhat narrow oval base; prickle color is between 200D and 165A often moderately suffused with between 201B and 201C. The major stem bears few small prickles of similar shape and coloration.

The color of the branches is between 146A and 137C sometimes moderately suffused with between 187B and 187A. The branches are rough in texture and they bear some large prickles which are of similar size and shape to the large prickles on the major stems; prickle color is near 161A. The branches bear few small prickles of similar shape and coloration.

The color of the new shoots is between 146B and 146C often heavily suffused with between 187B and 187A. The new shoots are rough in texture and they bear some large prickles which are of similar size and shape to the large prickles on the major stems; prickle color is between 152B and 152C usually heavily suffused with between 187B and 187C. The shoots bear few small prickles of similar shape and coloration.

The invention claimed is:

1. A new and distinct Shrub rose plant of the variety substantially as described and illustrated herein.

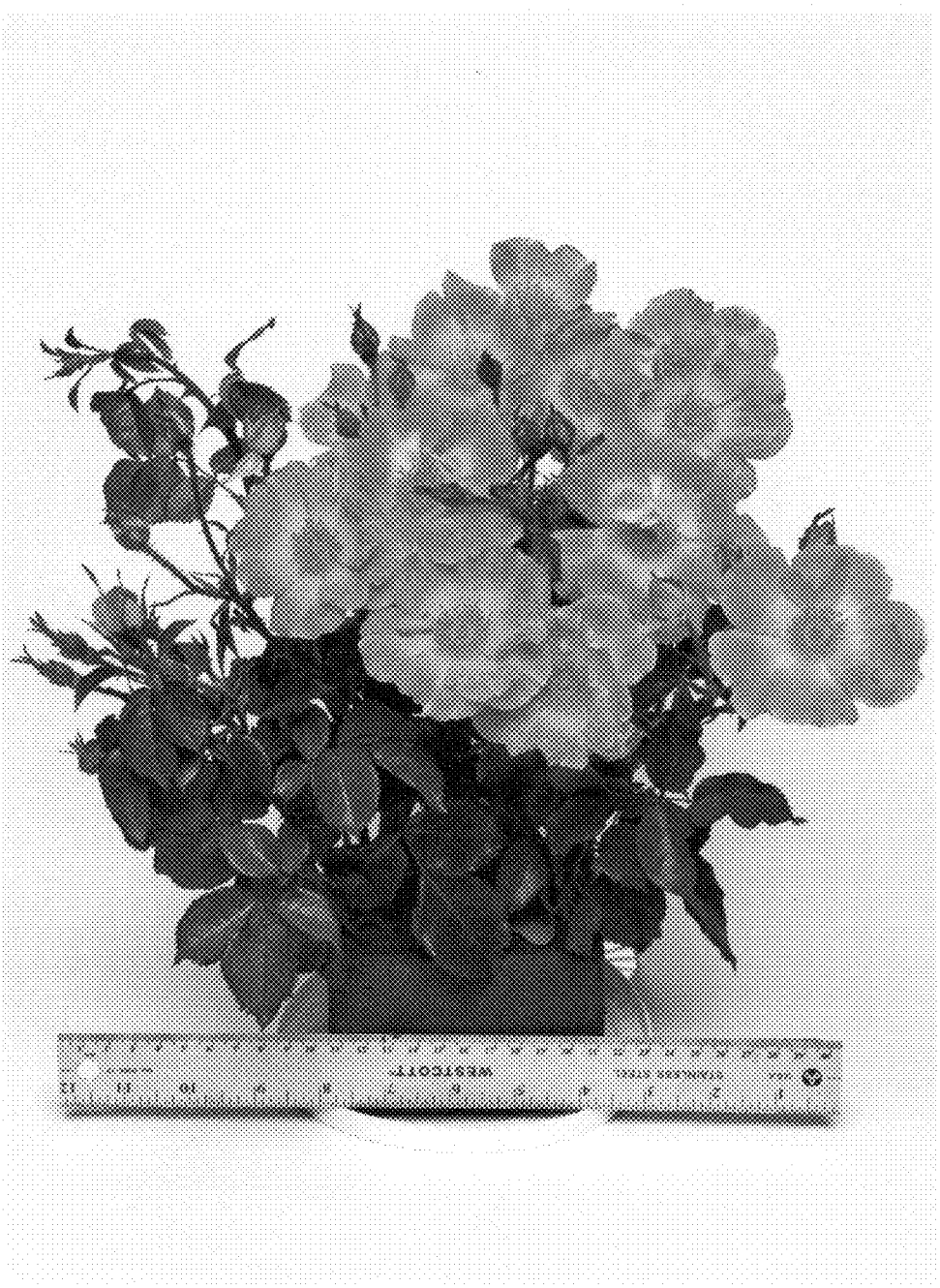

* * * * *